United States Patent [19]

Bitter et al.

[11] 4,347,377
[45] Aug. 31, 1982

[54] PROCESS FOR THE PREPARATION OF POLYHALOGENPHENYL CARBAMATES

[75] Inventors: Istvan Bitter; Rudolf Soos; Géza Tóth; László Töke; Gábor Szabo, all of Budapest, Hungary

[73] Assignee: Chinoin Gyogyszer es Vegyeszeti Termekek Gyara R.T., Budapest, Hungary

[21] Appl. No.: 188,966

[22] Filed: Sep. 19, 1980

[30] Foreign Application Priority Data

Sep. 14, 1979 [HU] Hungary .............................. CI 1963

[51] Int. Cl.³ .......................................... C07C 125/067
[52] U.S. Cl. ...................................... 560/32; 560/28; 560/29; 560/31; 560/132
[58] Field of Search .................. 564/276; 560/32, 132, 560/28, 29, 31

[56] References Cited

U.S. PATENT DOCUMENTS 4,042,582  8/1977  Papenfuhs .......................... 564/276

OTHER PUBLICATIONS

Le Clef et al., Angew. Chem., 85(10), 445–446, 1973; Angew. Chem. Internat. Edit., 12, 404–405 (1973).

Addor, J. Org. Chem., 29, 738–742, 1964.

*Primary Examiner*—G. T. Breitenstein
*Attorney, Agent, or Firm*—Karl F. Ross

[57] ABSTRACT

The invention concerns a new process for the preparation of polyhalogenphenyl carbamates of the formula (I)

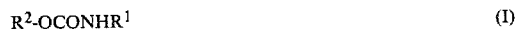

wherein
  $R^1$ is alkyl, aralkyl or aryl, where the aromatic rings may optionally be substituted; and
  $R^2$ is phenyl substituted with three, four or five halogens, through intermediates of the formula (IV)

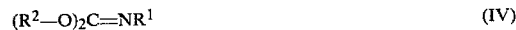

wherein $R^1$ and $R^2$ are as defined above.

The compounds of the formula (I) are valuable acylating agents. The intermediates of the formula (IV) are new compounds, which are also encompassed by the invention.

8 Claims, No Drawings

PROCESS FOR THE PREPARATION OF POLYHALOGENPHENYL CARBAMATES

This invention relates to a new process for the preparation of polyhalogenphenyl carbamates. More particularly, the invention concerns a new process for the preparation of polyhalogenphenyl carbamates of the formula (I)

$$R^2\text{-OCONHR}^1 \qquad (I)$$

wherein
R$^1$ is alkyl, aralkyl or aryl, where the aromatic rings may optionally be substituted; and
R$^2$ is phenyl substituted with three, four or five halogens.

According to the invention compounds of the formula (I) are prepared by
(a) reacting a compound of the formula (II)

$$R^1\text{-N}=CCl_2 \qquad (II)$$

wherein R$^1$ is as defined above, with a compound of the formula (III)

$$R^2\text{-OM} \qquad (III)$$

wherein R$^2$ is as defined above, and M is an alkali metal, and subsequently hydrolyzing a compound of the formula (IV)

$$(R^2\text{-O})_2C=NR^1 \qquad (IV)$$

obtained, wherein R$^1$ and R$^2$ are as hereinabove defined, in an acidic medium, with or without isolation; or
(b) hydrolyzing a compound of the formula (IV)

$$(R^2\text{-O})_2C=NR^1 \qquad (IV)$$

wherein R$^1$ and R$^2$ are as hereinabove defined, in an acidic medium.

The term "alkyl"—as such or in alkyl containing groups—as used throughout the specification relates to straight or branched chained saturated aliphatic hydrocarbon groups having 1 to 16, preferably 1 to 16, more preferably 1 to 4 carbon atoms, e.g. methyl, ethyl, isopropyl, isooctyl or tetradecyl groups.

The term "aryl" is used herein to refer to aromatic groups, having 7 to 10 carbon atoms, e.g. phenyl or naphthyl group, which may be substituted by one or more substituents selected from the group consisting of halogen, e.g. chlorine, fluorine, iodine or bromine; alkyl having 1 to 4 carbon atoms, e.g. methyl, ethyl, isopropyl or tert.-butyl; alkoxy having 1 to 4 carbon atoms, e.g. methoxy, ethoxy, isopropoxy; amino; alkylamino having 1 to 4 carbon atoms; or nitro.

The term "aralkyl" is used herein to identify goups, which are formed by the combination of aromatic groups having 7 to 10 carbon atoms, e.g. phenyl or naphthyl and alkyl groups having 1 to 6, preferably 1 to 4 carbon atoms. In the aralkyl groups the aromatic moiety may optionally be substituted by the same substituents which have been listed for "aryl" above.

The term "halogen" as used herein means fluorine, chlorine, bromine or iodine, preferably chlorine or bromine. Accordingly, R$^2$ may for example stand for trichlorophenyl, pentabromophenyl, etc. R$^1$ preferably stands for phenyl or tolyl, R$^2$ preferably represents trichlorophenyl or pentachlorophenyl and M preferably stands for potassium or sodium.

The polyhalogenphenyl carbamates of the formula (I) are known compounds, which can be widely used as acylating agents. Their activity is due to the phenyl group bearing three or more strongly electron-withdrawing substituents, i.e. halogens, which activates the carboxyl group. These so called active esters are capable of introducing a substituted carbamoyl group into hydroxyl and amino compounds under mild conditions [British Patent Specifications Nos. 1,460,057; 1,479,250; 9,346,953], and therefore can successfully be used for the preparation of numerous urea and carbamate derivatives, most of which are useful as plant protecting agents.

According to the known methods polyhalogenphenyl carbamates of the formula (I) can be prepared on the analogy of the processes known for the preparation of phenyl or thiophenyl esters [Liebig's Ann. Chem. 562, 219, 207 (1940); J. Org. Chem. 28, 658 (1963); Helv. Chem. Acta 48, 2005 (1965)], i.e.

(i.) by reacting polyhalogenphenols with isocyanates in the presence of basic catalysts; or (ii.) by reacting chloroformic acid phenyl ester (obtained by the reaction of polyhalogenated phenols with phosgene) with amines.

A common drawback of these methods consists in the fact that they—directly or indirectly—involve the use of phosgene which is highly toxic and can therefore be used only with extra precaution.

The compounds of the formula (II) used as starting materials in process variant (a) according to the invention are known in the art and can be prepared by simple methods with an excellent yield [Angew. Chem. 74, 861 (1962)].

The first step of process variant (a) is preferably carried out in a polar organic solvent, preferably acetone, dioxane, acetonitrile, dimethyl formamide, at 50° C. to 100° C. The alkali chloride formed in the first step can be eliminated by filtration and the intermediate of the formula (IV), if desired, can be isolated for example by distilling off the solvent.

The compounds of the formula (IV) used as starting materials in process variant (b) are new compounds, which can be prepared by reacting compounds of the formula (II) with compounds of the formula (III) under the reaction conditions described in connection with process variant (a).

The acidic hydrolysis of the compounds of the formula (IV) can be performed with mineral acids, preferably hydrochloric acid or a sulfonic acid.

The products can be isolated by conventional techniques, for example by filtration, and if desired, the polyhalogenated phenol can be regenerated by distilling off the solvent and subjecting the residue to an alkaline treatment and a subsequent acidification.

Further details of the invention are to be found in the following Examples. It is, however, by no means intended to limit our invention to the Examples.

EXAMPLE 1

N-Phenyl-pentachlorophenyl carbamate 17,4 g. (0.1 moles) of phenylisocyanide dichloride and 60.9 g. (0.2 moles) of pentachlorophenol potassium are boiled in 250 ml. of dioxane, potassium chloride is filtered off and the filtrate is evaporated. The residue is covered with isopropanol to yield a white crystalline substance, which is then boiled in a mixture of 100 ml. of isopropanol and 5 ml. of concentrated hydrochloric acid. The mixture is cooled to room temperature and the precipitated white crystalline substance is filtered off, washed with water and dried. The title compound, melting at 194° to 196° C. is obtained.

Analysis for $C_{13}H_6NO_2Cl_5$: calculated: C=40.40%, H=1.56%, N=3.63%; found: C=40.05%, H=1.51%, N=3.54%.

IR spectrum (KBr): 3290, 1740, 1600, 1520, 1390, 1200, 1010, 760, 600 cm$^{-1}$.

EXAMPLE 2

N-phenyl-trichlorophenyl carbamate 17.4 g. (0.1 moles) of phenylisocyanide dichloride and 47.1 g. (0.2 moles) of 2,4,6-trichlorophenol potassium are boiled in 250 ml. of dioxane. Furtheron the procedure described in Example 1 is followed to yield 12.6 g. (40%) of the title compound, melting at 134° to 136° C.

Analysis for $C_{13}H_8NO_2Cl_3$: calculated: C=49.20%, H=2.62%, N=4.42%; found: C=48.98%, H=2.56%, N=4.36%.

IR spectrum (KBr): 3310, 3080, 1740, 1600, 1535, 1450, 1225, 1140, 1000, 850, 695 cm$^{-1}$.

EXAMPLE 3

N-(m-Tolyl)-pentachlorophenyl carbamate 18.8 g. (0.1 moles) of m-tolyl-isocyanide dichloride and 60.9 g. (0.2 moles) of pentachlorophenol potassium are reacted as described in Example 1. The title compound is obtained with a yield of 62%. Melting pont: 187° to 189° C.

Analysis for $C_{14}H_8NO_2Cl_5$: calculated: C=42.05%, H=2.00%, N=3.51%; found: C=41.83%, H=2.03%, N=3.58%.

IR spectrum (KBr): 3290, 3040, 1735, 1610, 1525, 1385, 1225, 1030, 800, 770, 690 cm$^{-1}$.

We claim:

1. A process for the preparation of a polyhalogenphenyl carbamate of the formula $$R^2\text{-OCONHR}^1 \quad (I)$$

wherein $R^1$ is aralkyl or aryl in which the aromatic rings can be substituted: and $R^2$ is phenyl substituted with three, four or five halogens, which comprises reacting a compound of the formula $$R^1\text{-N}=CCl_2 \quad (II)$$

with a polyhalogen phenolate of the formula $$R^2\text{-OM} \quad (III)$$

wherein

M is an alkali metal, and subsequently hydrolyzing a compound of the formula $$(R^2\text{-O})_2C=NR' \quad (IV)$$

in an acidic medium, with or without isolation.

2. The process defined in claim 1, which comprises reacting a compound of the formula (II) with a compound of the formula (III) in an organic solvent.

3. The process defined in claim 2 in which as the organic solvent a polar organic solvent is used.

4. The process defined in claim 3 in which the polar organic solvent is acetone, dioxane, acetonitrile or dimethyl formamide.

5. The process defined in claim 3 wherein the reaction is carried out at a temperature of 50° C. to 100° C.

6. The process defined in claim 1, which comprises carrying out the acidic hydrolysis with a mineral acid.

7. A process as claimed in claim 6 in which hydrochloric acid or sulfonic acid is used as the mineral acid.

8. A process for the preparation of a polyhalogenphenyl carbamate of the formula $$R^2\text{-OCONHR}^1 \quad (I)$$

wherein $R^1$ is aralkyl or aryl and $R^2$ is phenyl substituted with three, four or five halogens, which comprises the step of hydrolyzing a compound of the formula $$(R^2\text{-O})_2C=NR^1 \quad (IV)$$

in an acidic medium.

* * * * *